United States Patent
Cornelius et al.

(10) Patent No.: US 10,431,339 B1
(45) Date of Patent: Oct. 1, 2019

(54) METHOD AND SYSTEM FOR DETERMINING RELEVANT PATIENT INFORMATION

(71) Applicant: EPIC Systems Corporation, Verona, WI (US)

(72) Inventors: Aaron T. Cornelius, Mount Horeb, WI (US); Nate C. Peterson, Madison, WI (US)

(73) Assignee: EPIC Systems Corporation, Verona, WI (US)

(*) Notice: Subject to any disclaimer, the term of this patent is extended or adjusted under 35 U.S.C. 154(b) by 562 days.

(21) Appl. No.: 14/742,951

(22) Filed: Jun. 18, 2015

Related U.S. Application Data

(60) Provisional application No. 62/014,589, filed on Jun. 19, 2014.

(51) Int. Cl.
*G16H 50/20* (2018.01)
*G16H 10/60* (2018.01)

(52) U.S. Cl.
CPC ............. *G16H 50/20* (2018.01); *G16H 10/60* (2018.01)

(58) Field of Classification Search
CPC ..... G06F 19/345; G06F 19/322; G16H 50/20; G16H 10/60
See application file for complete search history.

(56) References Cited

U.S. PATENT DOCUMENTS

| | | |
|---|---|---|
| 7,716,072 B1 | 5/2010 | Green et al. |
| 7,774,210 B1 | 8/2010 | Sandberg |
| 2007/0162310 A1 | 7/2007 | Schmidt |
| 2011/0202486 A1* | 8/2011 | Fung ................... G06F 19/3431 706/12 |
| 2013/0096941 A1* | 4/2013 | Kanada ................. G16H 50/70 705/2 |
| 2013/0231953 A1* | 9/2013 | Ebadollahi ............. G06Q 50/22 705/3 |
| 2014/0058754 A1 | 2/2014 | Wild |
| 2014/0207802 A1* | 7/2014 | Raghavan ......... G06F 17/30958 707/749 |
| 2015/0269691 A1 | 9/2015 | Bar Yacov et al. |

OTHER PUBLICATIONS

Non-Final Office Action on U.S. Appl. No. 14/484,690 dated Apr. 24, 2017.
Final Office Action on U.S. Appl. No. 14/484,690 dated Nov. 20, 2017.

* cited by examiner

*Primary Examiner* — Christopher L Gilligan
(74) *Attorney, Agent, or Firm* — Foley & Lardner LLP

(57) ABSTRACT

Media, methods, and systems facilitate identification and presentation of medical information that is relevant to a current condition of a patient. The relative prominence of the information is associated with the relative relevance of the information with the current condition. A weighted graph is used to determine the relevance.

20 Claims, 9 Drawing Sheets

700

```
Anatomy: Left Arm
                         Related Anatomy
Laterality: Left

Related Anatomy              Type                  Weight
27. 11136-Left Humerus        Descendant            .97
28. 11158-Left Long Biceps Tend*  Descendant        .97
29. 11186-Left TFCC           Descendant            .96
30. 10086-Cervical Spine      Adjacent              .75
31. 10056-Thoracic Spine      Adjacent              .75
32. 11129-Right Arm           Contralateral         .5
33. 11127-Right Shoulder      Contralateral Desc*   .49
34. 11131-Right Upper Arm     Contralateral Desc*   .49
35. 11133-Right Forearm       Contralateral Desc*   .49
36. 11135-Right Elbow         Contralateral Desc*   .49
37. 11101-Right Scapula       Contralateral Desc*   .48
38. 11125-Right Clavicle      Contralateral Desc*   .48
39. 11139-Right Common Flexor T*  Contralateral Desc*  .48

<F6> - Edit Override Settings
           <F8> - Jump to Related Anatomy Record
```

FIG. 7

METHOD AND SYSTEM FOR DETERMINING RELEVANT PATIENT INFORMATION

CROSS-REFERENCE TO RELATED APPLICATIONS

This application claims priority to U.S. Provisional Application No. 62/014,589 filed Jun. 19, 2014, the contents of which are incorporated by reference in its entirety into the present disclosure.

BACKGROUND

The advent of electronic medical records and networking capabilities for sharing these records has greatly increased the amount of patient information available to caregivers. While this availability of information has given caregivers more opportunity to recognize relevant trends and connections in a patient's medical history, the sheer amount of information can sometimes cause relevant or vital information to be hidden among less important records. Even when a caregiver is able to effectively locate the vital information, precious time may be lost reviewing the patient's full medical history for relevant information.

SUMMARY OF THE DISCLOSURE

The presently disclosed embodiments may help to facilitate easier review of patient medical information by providing highly relevant information. Additionally, the embodiments may present relevant information more prominently in accordance with the information's relevance to the current condition of the patient.

In one embodiment, an example computer readable medium stores instructions that a processing system may execute in order to perform certain functions. The functions include receiving data indicating a patient's identity and a current condition associated with the patient. The functions also include using a weighted graph to determine a relevance score representing the relevance, to the current condition, of historical patient information associated with the patient. In the weighted graph, the current condition and the historical patient information are each represented by respective nodes.

In another embodiment, an example method includes receiving data indicating a patient's identity and a current condition associated with the patient. The method also includes using a weighted graph to determine a relevance score representing the relevance, to the current condition, of historical patient information associated with the patient. In the weighted graph, the current condition and the historical patient information are each represented by respective nodes.

In another embodiment, an example processing system includes a processor, a computer readable medium, and a communication interface. The processor is configured to receive data indicating a patient's identity and a current condition associated with the patient. The processor is also configured to use a weighted graph to determine a relevance score representing the relevance, to the current condition, of historical patient information associated with the patient. In the weighted graph, the current condition and the historical patient information are each represented by respective nodes.

The foregoing is a summary and thus by necessity contains simplifications, generalizations and omissions of detail. Consequently, those skilled in the art will appreciate that the summary is illustrative only and is not intended to be in any way limiting. Other aspects, inventive features, and advantages of the devices and/or processes described herein, as defined by the claims, will become apparent in the detailed description set forth herein and taken in conjunction with the accompanying drawings.

BRIEF DESCRIPTION OF THE DRAWINGS

FIG. 7 is a table showing example weight and hierarchal data according to an exemplary embodiment.

DETAILED DESCRIPTION

Referring generally to the figures, systems and methods are described herein for facilitating the identification and intelligent presentation of patient information that is relevant to a current patient condition.

The following disclosure is divided into three main sections. The first section discusses the devices and systems that can be used in an example embodiment. The second section discusses the techniques and methods involved in an example embodiment. The third section discusses a particular embodiment of the present systems/method relating to orthopedics. Although the section on example methods references elements from the example system section, this is not intended to imply that the example systems and methods must be used together. Rather, the example methods may be carried out using any suitable system or combination of systems and the described example systems may carry out procedures other than those outlined in the example methods.

I. Example System Architecture

Functions and procedures described herein may be executed according to any of several embodiments. For example, procedures may be performed by specialized equipment that is designed to perform the particular functions. As another example, the functions may be performed by general-use equipment that executes commands related to the procedures. As still another example, each function may be performed by a different piece of equipment with one piece of equipment serving as control or with a separate control device. As a further example, procedures may be specified as program instructions on a computer-readable medium.

Figure 1:
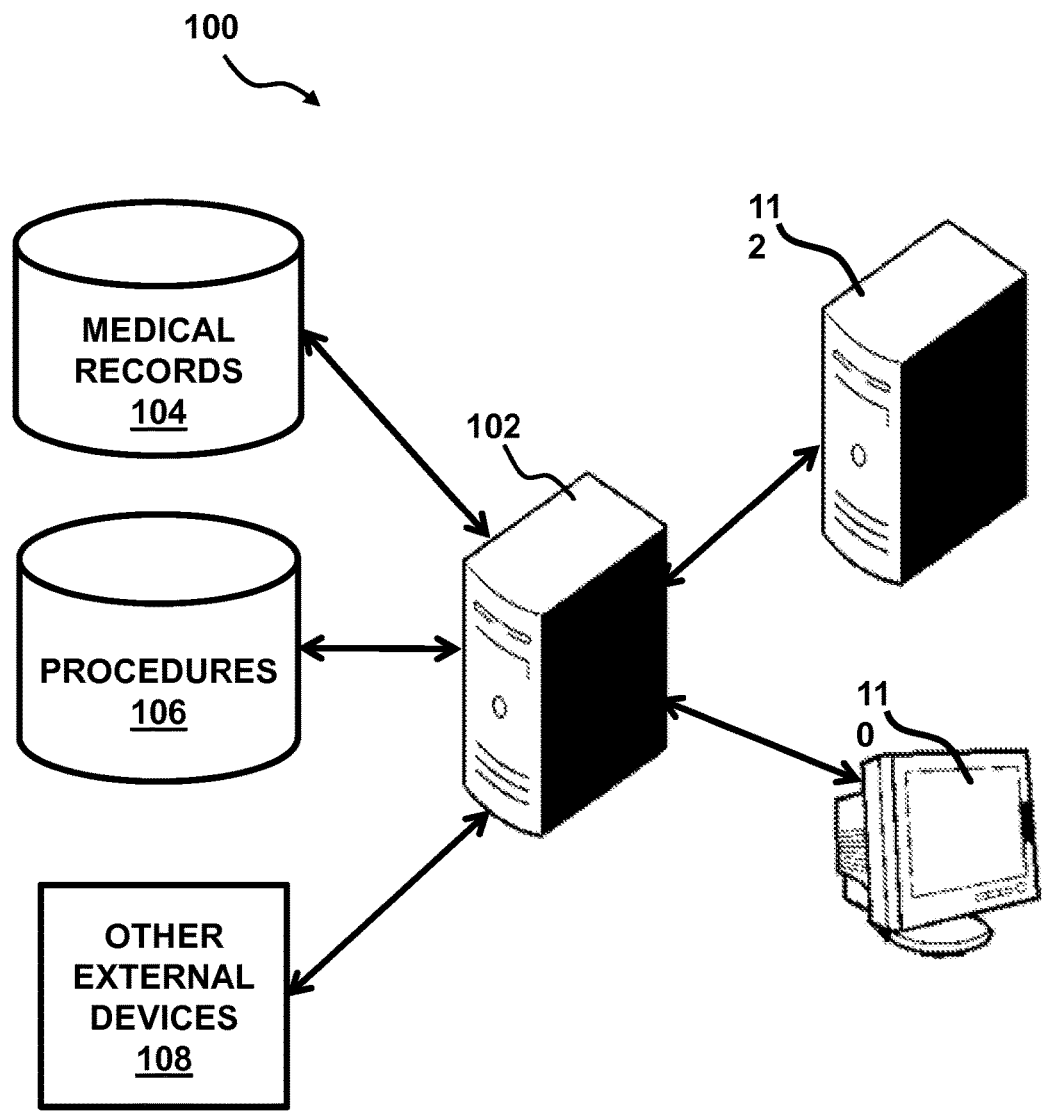
FIG. 1 is a schematic illustrating elements of an example network, according to an example embodiment.

FIG. 1 shows a networked system 100 according to an exemplary embodiment. As shown, the system includes a processing system 102 communicatively coupled to a set of remote and/or local devices. In some embodiments, like the network shown in FIG. 1, processing system 102 may connect to various output systems, such as display device 110 and server 112. Processing system 102 may also connect with various information input devices, such as external storage (Medical Records 104), procedure storage 106, and/or other external devices/systems 108. Communicative links are formed between each of the elements of system 100. Such links may be any type of communicative connection. For example, the connections may be wired electrical connections, wireless connections, fiber-optic connections, air interfaces, or acoustic transmission networks.

Processing system 102 may be any generalized computing device that stores instructions for carrying out an exemplary process. Alternatively, processing system 102 may be a specialized computing device configured to perform the certain functions needed using hardware. In still other embodiments, processing system 102 may be a set of various computing devices, either performing the same function or each configured to perform a specific function. Processing system 102 may typically include a non-transitory computer-readable medium, processor, and communication interfaces among other example components, as described with reference to FIG. 2.

Display device 110 may be any of various device types. Display device 110 may be associated with one or more network locations on any of various communication networks. For example, if display device 110 is a cellular phone, then the network address may be a telephone number and the notification system may access a landline or cellular telephone network to contact display device 110. As another example, if display device 110 is an Internet-enabled computing device, then the network location may be a registration node on an email, VoIP, or other registration server with which the notification system may communicate over various data links. Any presently known or future device capable of these functions may be used as display device 110. Some non-limiting examples include e-readers, tablets, laptops, smartphones, video phones, televisions, desktop computers, PDAs, pagers, and/or fax machines.

As will be explained more below, processing system 102 may receive patient data from various sources. Although FIG. 1 shows three main types of information sources, this illustration is not meant to be limiting. Medical information may be received in ways other than those explicitly shown and described. As shown in FIG. 1, processing system 102 may receive data from, and transfer data to external storage in the form of medical records and procedures. Medical records 104 may store previously determined health information for continually updated information from sources not directly connected to processing system 102. Procedures storage 106 may store instructions, data structures, conversion factors, and raw data necessary for preforming the present functions. In some cases, procedures storage 106 may store the weighted graph of conditions.

Figure 2:
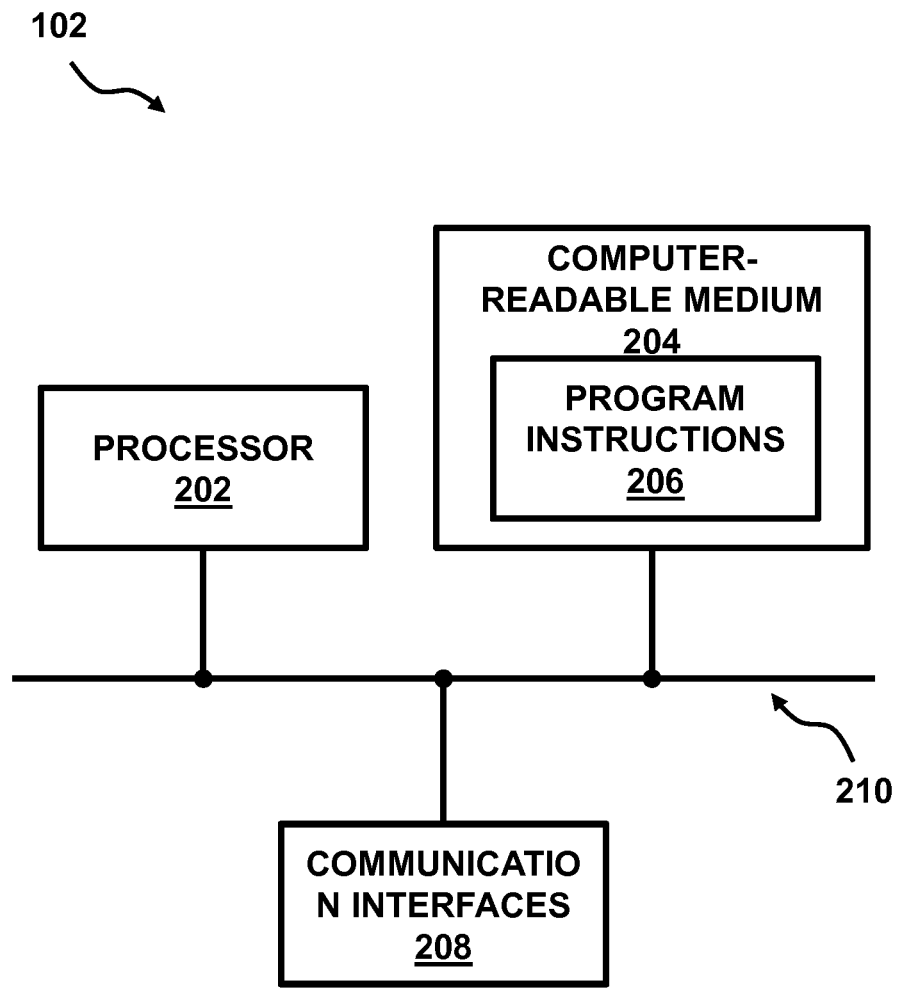
FIG. 2 is a schematic illustrating elements of an example processing system according to an example embodiment.

One example processing system (102) is shown in FIG. 2. As shown, processing system 102 includes a processor 202, a computer-readable medium (CRM) 204, and communication interfaces 208, all connected through system bus 210. Also as shown, program instructions 206 are stored on computer-readable medium 204. In the present disclosure, this device may be seen as an embodiment of processing system 102.

Processor 202 may include any processor type capable of executing program instructions 206 in order to perform the functions described herein. For example, processor 202 may be any general-purpose processor, specialized processing unit, or device containing processing elements. In some cases, multiple processing units may be connected and utilized in combination to perform the various functions of processor 202.

CRM 204 may be any available media that can be accessed by processor 202 and any other processing elements in device 102. By way of example, CRM 204 may include RAM, ROM, EPROM, EEPROM, NAND-based flash memory, CD-ROM, Bluray, or other optical disk storage, magnetic disk storage or other magnetic storage devices, or any other medium that can be used to carry or store desired program code in the form of program instructions or data structures, and which can be executed by a processor. When information is transferred or provided over a network or another communications connection (either hardwired, wireless, or a combination of hardwired or wireless) to a machine, the machine properly views the connection as a CRM. Thus, any such connection to a computing device or processor is properly termed a CRM. Combinations of the above are also included within the scope of computer-readable media.

Program instructions 206 may include, for example, instructions and data capable of causing a processing unit, a general-purpose computer, a special-purpose computer, special-purpose processing machines, or remote server systems to perform a certain function or group of functions.

Communication interfaces 208 may include, for example, wireless chipsets, antennae, wired ports, signal converters, communication protocols, and other hardware and software for interfacing with external systems. For example, device 102 may receive text, audio, executable code, video, digital information or other data via communication interfaces 208 from remote data sources (e.g., remote servers, internet locations, intranet locations, wireless data networks, etc.) or from local media sources (e.g., external drives, memory cards, specialized input systems, wired port connections, wireless terminals, etc.). Example communication networks include Public Switched Telephone Network (PSTN), Public Switched Data Network (PSDN), a short message service (SMS) network, a local-area network (LAN), a voice over IP (VoIP) network, a wide area networks (WAN), a virtual private network (VPN), a campus area network, and the Internet. An example network may communicate through wireless, wired, mechanical, and or optical communication links. Many other communication networks may also be suitable for the embodiments discussed herein.

Communication interfaces 208 may include user-interfaces to facilitate receiving user-input and user-commands into device 102 and outputting information and prompts for presentation to a user. Although such interfaces typically connect with human users, user-interface 212 may alternatively connect to automated, animal, or other non-human "users." Additionally, while input and output are described herein as occurring with a user present, user-interface 212 need not present information to any actual user in order for present functions to be performed. User-input may be received as, for instance, wireless/remote control signals, touch-screen input, actuation of buttons/switches, audio/speech input, motion input, lack of interaction for a pre-defined time period, and/or other user-interface signals. Information may be presented to the user as, for instance, video, images, audio signals, text, remote device operation, mechanical signals, media file output, etc. In some cases, separate devices may be operated to facilitate user-interface functions.

An example system may also include a variety of devices or elements other than those shown in FIG. 2. For example, device 102 may include visual displays or audio output devices to present results of an example process. As another example, CRM 204 may store computer applications for specific data-generation or data-processing functions. Other examples are possible.

II. Example Methods

Figure 3:
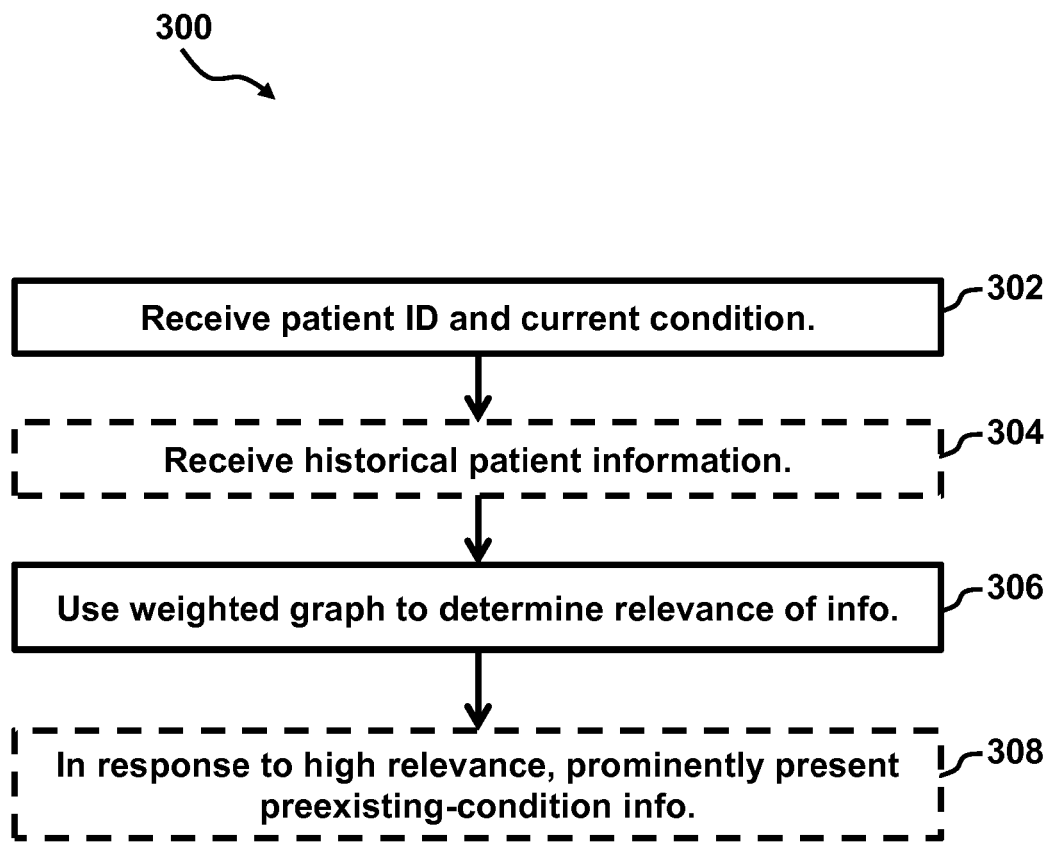
FIG. 3 is a block diagram illustrating a method according to an example embodiment.

FIG. 3 illustrates a method 300 according to an example embodiment. Although the figure shows a specific order of method steps, the order of the steps may differ from what is depicted. Also, two or more steps may be performed concurrently or with partial concurrence. Such variations may depend on the software and hardware systems chosen and the specific embodiment. All such variations are within the scope of the disclosure. Likewise, software implementations could be accomplished with standard programming techniques with rule-based logic and other logic to accomplish the various connection steps, processing steps, comparison steps and decision steps.

A. Identifying and Presenting Relevant Information

As shown at block 302, method 300 includes receiving data representing a patient's identity and a current health condition for the patient. A computing device or system, such as system 102, may receive data from a variety of sources and the received data may include various types of information. In some cases, data may be received from a single source all at once. In other cases, data may be received from several sources and/or over several receiving steps. Medical data may be received, for example, via communication interfaces 208 from local or remote external sources, such as sources 104, 106, and 108. In some cases, data may be received periodically. In other cases, the data may be received through a synchronous or asynchronous push operation from the external sources or pull operation from system 102. In some embodiments, the source of observed data may be the originator of such data (e.g., medical monitor, lab system, sensing device, input device, etc.).

Figure 4:
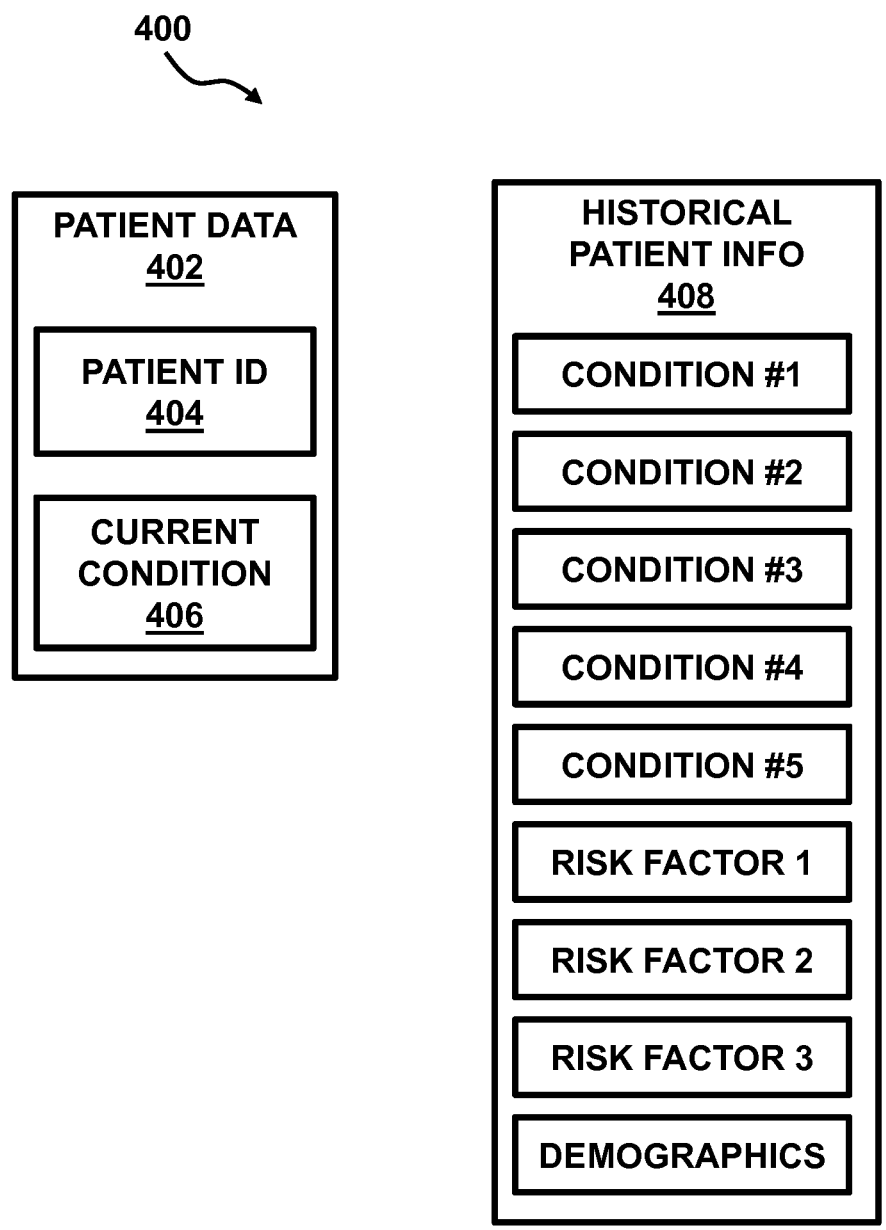
FIG. 4 is a block diagram illustrating received data structures according to an example embodiment.

FIG. 4 shows a particular example of a format in which patient data 402 may be structured upon receipt. In particular, patient data 402 includes one variable or data structure that is indicative of patient identification (ID) information 404 and a separate stored data structure indicative of a current condition 406 associated with the patient. The structure is merely a point of reference and should not be seen as limiting as other data structure may be used.

Although the singular term "current condition" may be used throughout the present disclosure, current condition 406 may include multiple particular conditions, diagnoses, and attributes of the patient and/or a medical visit of the patient. In some embodiments, a system that receives multiple current conditions for a patient may select a single condition as the primary concern for a medical visit. In other embodiments, the system may combine the set of current conditions to form a condition group based on the set of current conditions. The system may automatically perform either of these procedures based on stored instructions, or it may prompt a user for instructions on how to deal with the multiple current conditions. In some situations, the conditions related to the current visit (facility, caregiver, time/day of visit, etc.) may be used as indicative of a "current condition" of the patient. For example, if the user wishes to access relevant information prior to receiving any reason for the visit, then the system may use this supplementary condition information in determining relevance.

In one example embodiment, other external devices 108 may include a computer operated by a patient receiving team. When the patient checks in with the receiving team, receiving staff may ask the patient or attending personnel (EMTs, family, police, etc.) for patient identification information 404 related to the patient (e.g., name, address, Social Security number, insurance information, primary care network, birthdate, etc.) and information about the patient's current condition 406. Current condition 406 may be, for example, an explanation from the patient about the reason for their visit to the medical facility, a description of the patient's medical issues from attending personnel, data obtained upon admittance of a patient (e.g., blood pressure, pulse, weight, etc.), or any other information relevant to a patient's current condition. In some cases, the requested identification information for the patient may be stored as the key (name) for the received data. In other cases, the identification information may be used to find the particular identifier that the system already uses to identify the patient. In this way, any new information about the patient may be associated with existing patient information, without unnecessarily revealing confidential medical information to medical staff or caregivers.

In some cases, current condition 406 of the patient may be inferred from stored information on the system (e.g., in CRM 204) or in an external memory (e.g., in medical records 104). For example, the system may already have a stored reason for the patient's visit, as in the case of a follow-up visit for a problem that a doctor has already diagnosed. As another example, the particular type of appointment may dictate a certain condition (e.g., an appointment with a specialist may be associated with their specialty or an appointment for a lab test may be associated with conditions that would require such tests.)

Although many of the example situations described herein relate to the situation of a patient coming to a medical center while experiencing the "current condition," the present methods may be equally applied to other situations. For example, if a doctor receives the results of a patient's lab test, then this doctor would have a need to quickly locate information relevant to a condition indicated by the test results. As another example, if a researcher wishes to investigate a patient's medical history with regard to a particular medical condition (either current or former), then current condition 406 may be the condition that the researcher is currently investigating. As a further example, a patient who is worried about a potential medical condition may wish to review their own medical records in light of this potential condition (i.e., before receiving a prognosis).

Current condition 406 for the patient may represent any type of medical disease, injury, procedure, test result, complaint, anomaly, or other health-related conditions. For example, some common medical diagnoses are listed in classification standards like the ICD-9, ICD-10, DSM-IV, EUROCAT, READ, and SNoMed-CT, which classify diseases and health-related conditions or problems. As another example, standard medical procedures are listed in procedural classifications such as HCPCS, ICD-10-PCS, ICHI, and ICPC, among other examples. Other example standard classifications include Nursing Intervention and Outcome Classification, LOINC, and MeSH terminology standard. In addition to the standardized medical conditions from industry-standard classifications, medical professionals may diagnose or derive their own condition classifications, based on experience. For example, if a patient's medical condition is either undiagnosed or unknown, the caregiver (or the system) may collect the various characteristics of the condition (symptoms, lab results, similarities to other known conditions, etc.) and use these to define a derived current condition. In some embodiments, the term preexisting may refer to the fact that the condition is either a former condition, a continuing condition, or a new condition that is not current condition 406. The term preexisting should not necessarily be limited to those medical conditions that the patient no longer experiences.

As shown at block 304, method 300 may include receiving historical patient information associated with the patient. As indicated by the dashed lines in FIG. 3, an example embodiment need not necessarily include such receiving. In some cases, the historical patient information may be associated with a preexisting condition of the patient. Like the current condition, a preexisting condition may be any type of condition or characteristic of the patient that could be relevant to a health professional. In addition to preexisting conditions, patient information may also be associated with family medical history, personal medical history, risk factors, genetic data, or demographic information. As with the current condition, the historical patient information may be received from a variety of internal or external sources. In some cases, the information may be previously stored at the processing system and need not be received. Historical information may represent any information that was collected prior to the time of searching for relevant information. Therefore, if a physician receives a patient's current height and blood pressure readings that a nurse collected only minutes ago, this information may either factor into the current condition or the historical information depending on the needs or preferences of the user. In a typical situation, the historical patient information may be included in an overall patient's medical history. For instance, FIG. 4 shows an example format of the received medical history 408, including several preexisting conditions (labeled "CONDITION #1"-"CONDITION #5"), several risk factors ("RISK FACTOR 1"-"RISK FACTOR 3"), and demographic information ("DEMOGRAPHICS".) In an example embodiment, the system may sequentially or simultaneously compare each piece of received of patient information to current condition 406 as will be described. Accordingly, the process described with respect to the single piece of historical patient information may be a single iteration of the larger process. Additionally, other medical information, such as family medical histories, current treatments, patient location, etc. may be received with the patient records.

In some cases, the system may request the patient's medical history in response to receiving the patient ID and current condition. In other cases, the medical records may be periodically sent to the system. In still other cases, the medical records may be received along with the current condition and ID. In this last example, the received data 400 in FIG. 4 may be considered to be a single dataset. The received data in such an implementation may be structured as a single list of conditions, with the current condition being listed with the other historical patient information.

Once the history is received, the system may divide the history into potentially relevant pieces of information. The conditions may be divided according to standard classifications, caregiver preferences, and/or semantic segmentation based on language cues in the history. In some embodiments, the system may already maintain segmentations in the medical file that divide out different pieces of information. In order to process the received information, the system may need to determine what condition each segment of information may indicate. For example, results of a blood test may be indicative of a certain disease, but the system may need to identify the disease before other procedures are performed. In other embodiments, the system may only require indications of the symptoms/characteristics, precluding the need for identifying the condition.

In some embodiments, the historical medical information may include conditions that are not yet diagnosed, but with which other historical information and current conditions are often associated. For example, if a certain condition is highly relevant to several conditions that the patient has, especially if the diagnosed conditions are rarely co-present in patients that do not have the undiagnosed condition, then the system may present the condition as a potential preexisting condition. Additionally, the undiagnosed condition may be presented prominently in response to determining that diagnosed conditions are part of a family of conditions with the undiagnosed condition. If a caregiver then accesses the potential condition, the system may present the connected conditions that seem to indicate the presence of the undiagnosed condition. Even if the patient does not have the undiagnosed condition, the condition may be presented due to a preexisting high risk for developing the undiagnosed condition. In this sense, the risk is the historical patient information, and the risk is highly related to an actual condition.

As shown at block 306, method 300 may include using a weighted graph to determine the relevance of the historical patient information. A graph is a data structure, in this case accessible by a computing/processing system, in which data points, called "nodes," are linked to one another through defined connections, called "edges." In the weighted graph, each of the edges is associated with a particular "weight" (e.g., a coefficient, additive constant, ratio, etc.) that represents some intrinsic quality of the data represented by the nodes. For example, a geographic map could be digitally represented by a weighted graph, with the nodes representing locations, the edges representing routes between the locations, and the weight of each edge indicating a distance of the route. In the mapping example, an input to the weighted graph may be a starting and ending node (location) and an output may be the shortest distance between the nodes.

Figure 5:
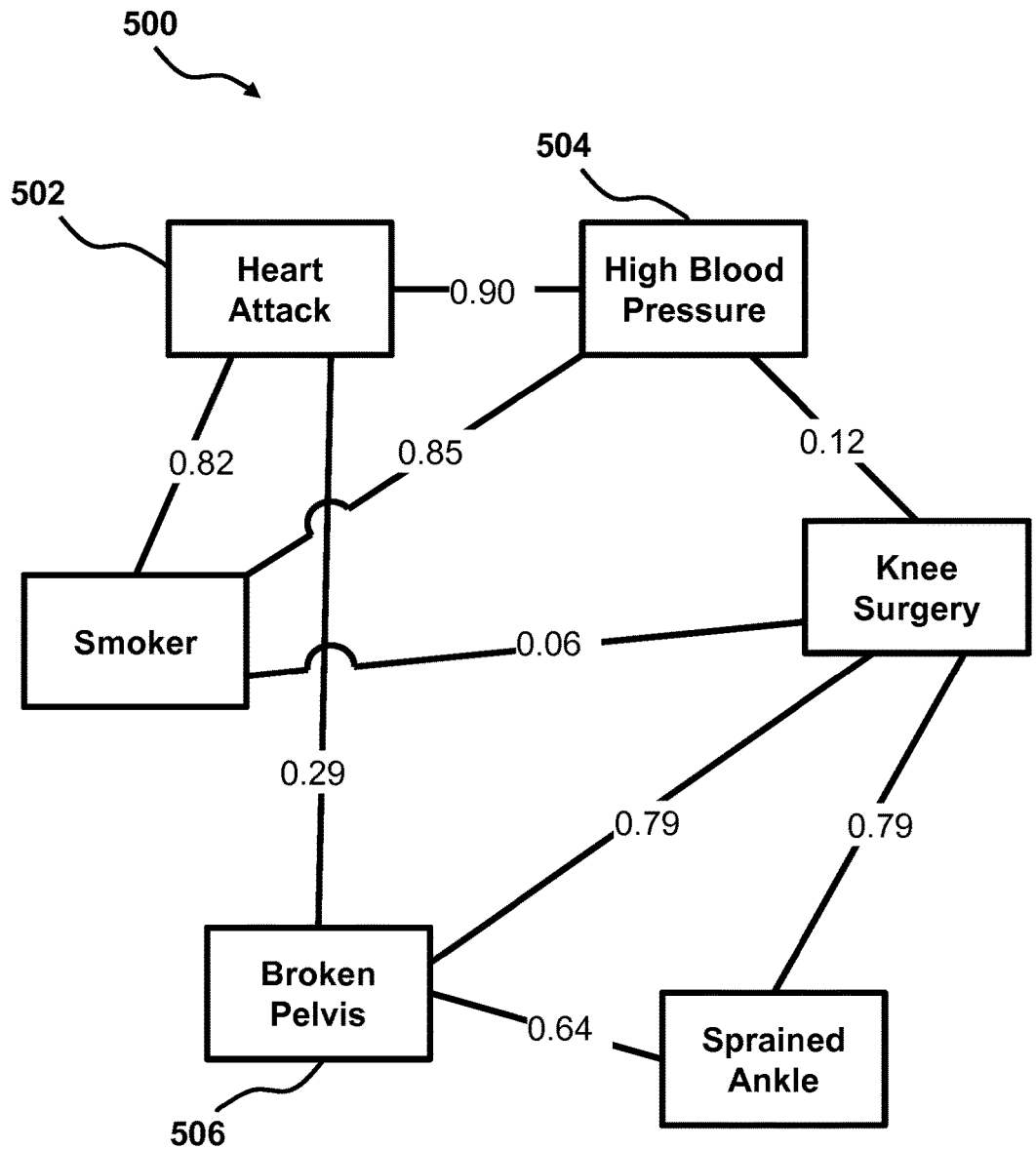
FIG. 5 is a block diagram representing a weighted graph according to an example embodiment.

In the present embodiments, each of the nodes in the weighted graphs may represent a piece of medical information that may be associated with a patient and the edges may represent the relevance of one condition to another. FIG. 5 shows a particular example of a weighted graph of medical conditions in accordance with an example embodiment. The conditions, connections, and weights shown in FIG. 5 are examples. In the embodiment of FIG. 5, the weights are represented by coefficient values between "0" and "1." In this arrangement, the relevance of one condition to another may be close to "1" if the two conditions are highly interdependent and close to "0" if the conditions are not related at all. Other weighting systems may be applied equally as well, including all integers, decimals, fractions, categories, etc. Although weighted graph 500 is an incomplete graph (i.e., there are nodes that do not connect directly), an example system may use a complete graph (i.e., an edge and weight is assigned to every possible connection between nodes). Additionally, although the weighted edges are shown as unidirectional, some weighted graphs may include directionally dependent edges (i.e., edges that only connect in a certain direction from one node to another).

In a complete and directionally dependent weighted graph, every possible connection between nodes would include two edges, one for each direction, so that a weight may be assigned for each direction. Such a weighted and directional implementation allows the system to establish a hierarchy, or family-tree type relationship between different conditions. For example, if the body is represented by a weighted graph, as will be explained in more detail hereinafter, then conditions related to the outer extremities may be considered descendent conditions to similar conditions to the inner extremities. In one embodiment, the system may treat a patient's injuries to their left shoulder, left forearm, and left thumb as a family of conditions, in which the shoulder injury is the "ancestor" to the forearm injury and the forearm injury is ancestor to the thumb injury. The weighted directional graphs may be useful in such a situation, because information related to previous ancestor injuries may be more relevant to current descendent injuries than information related to the descendent injuries is to current ancestor injuries. For instance, if a forearm injury is the current condition, then, while both the shoulder and thumb injuries are probably relevant, the ancestor injury (the shoulder) may be more important for the doctor to recognize to avoid exacerbating the preexisting condition. Similar hierarchical relationships may be formed with respect to many medical conditions.

Current conditions, preexisting conditions, and other health information may be grouped in some cases to express particular relationships between information. For example, conditions, treatments, and procedures that are diagnosed, prescribed, or performed by a particular caregiver may be linked to a node representing that caregiver. As another example, medical information from a single visit may be linked to a node representing that visit. As still another example, medical visits that occur at one medical facility, or in one department at a facility, may be linked to a node representing that facility or department. Connections between the group nodes may be made and weighted so that these groupings may also contribute to the relevance of the medical information.

As a specific example, a doctor that has already had one or two visits with a patient may wish to have information that was created at those visits be more relevant than information from visits with other doctors. As another example, if the current condition is related to a malady that most commonly occurs during the winter, then information associated with visits during the winter may be deemed more relevant. As still another example, if the caregiver has positive experiences with one of the departments that previously treated the patient, then the caregiver may indicate that information from that department be more relevant than information from other departments.

Within each grouping, different weights may be assigned to the connections between the group node and the individual pieces of information. Such differences in weighting may result from some information being indicated, for example, as more relevant or important by the physician on duty. As another example, if a treatment prescribed by a certain doctor was actually suggested by a nurse, other staffer, or automated system, then the system may be programmed to assign a lower weighting to the connection between the caregiver node and the treatment. In the case that an automated system offers potential diagnoses and/or recommends treatments, the system may automatically track whether the diagnoses and treatments for a visit were offered by the system or directly by the physician. In this way, the weights may be adjusted automatically, without requiring the physician to manually enter how a diagnosis was made. Other example situations reasons may be used for determining weights either among grouping nodes or between information nodes and grouping nodes.

Information other than just a weight and direction may also be conveyed through edges. For example, an edge that leads to a piece of diagnosis information may have a category or type of "diagnosis" associated directly with the connection. When the system is assessing the relevance of the diagnosis information, the categories or types associated with the various edges may be used to determine relevance scores. For example, a program may specify that only three diagnoses may be displayed as relevant information. In this way, various features of the weighted graph may be assessed automatically as the system moves through the weighted graph.

Figure 8:
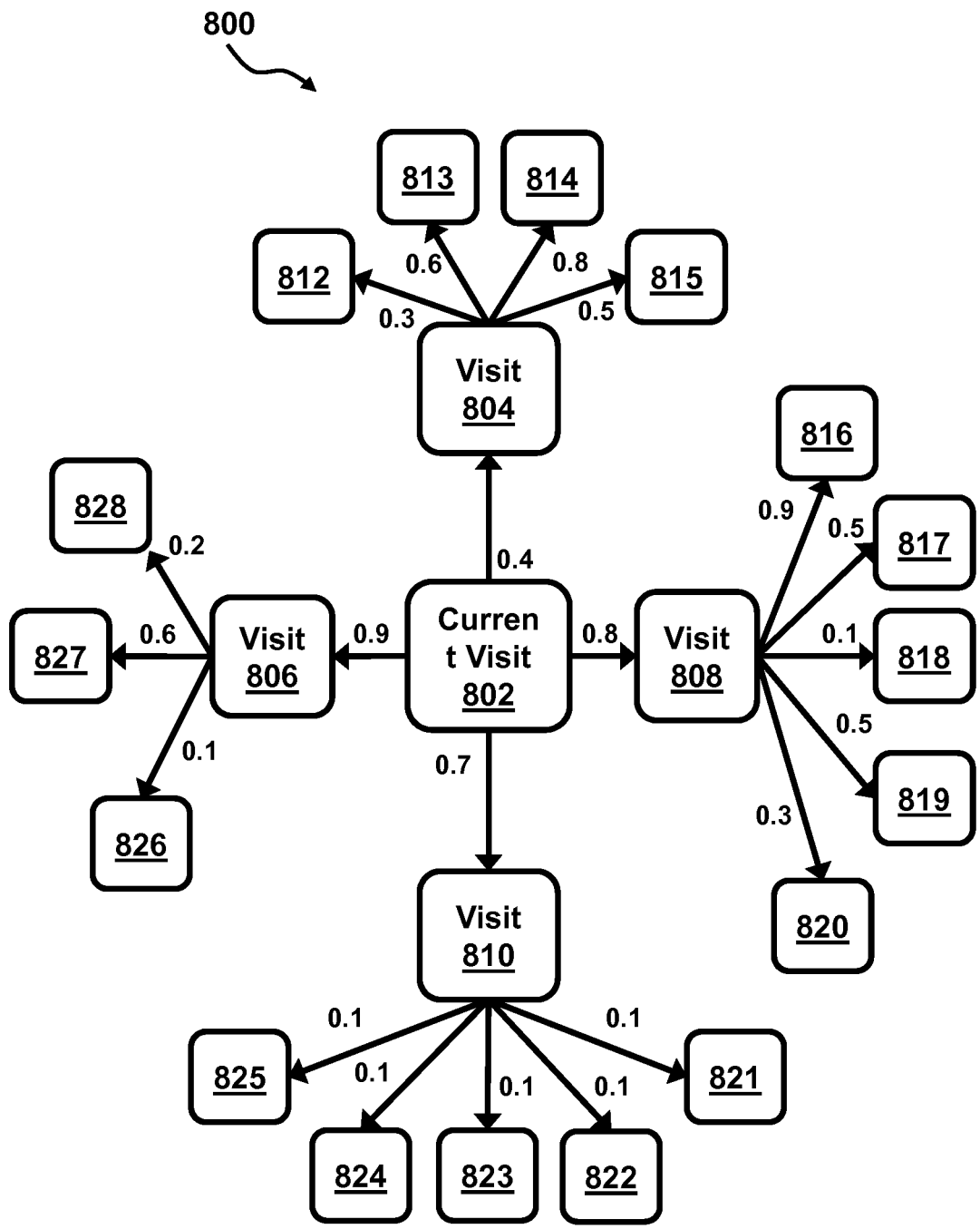
FIG. 8 is a first example weighted graph that utilize group nodes.
Figure 9:
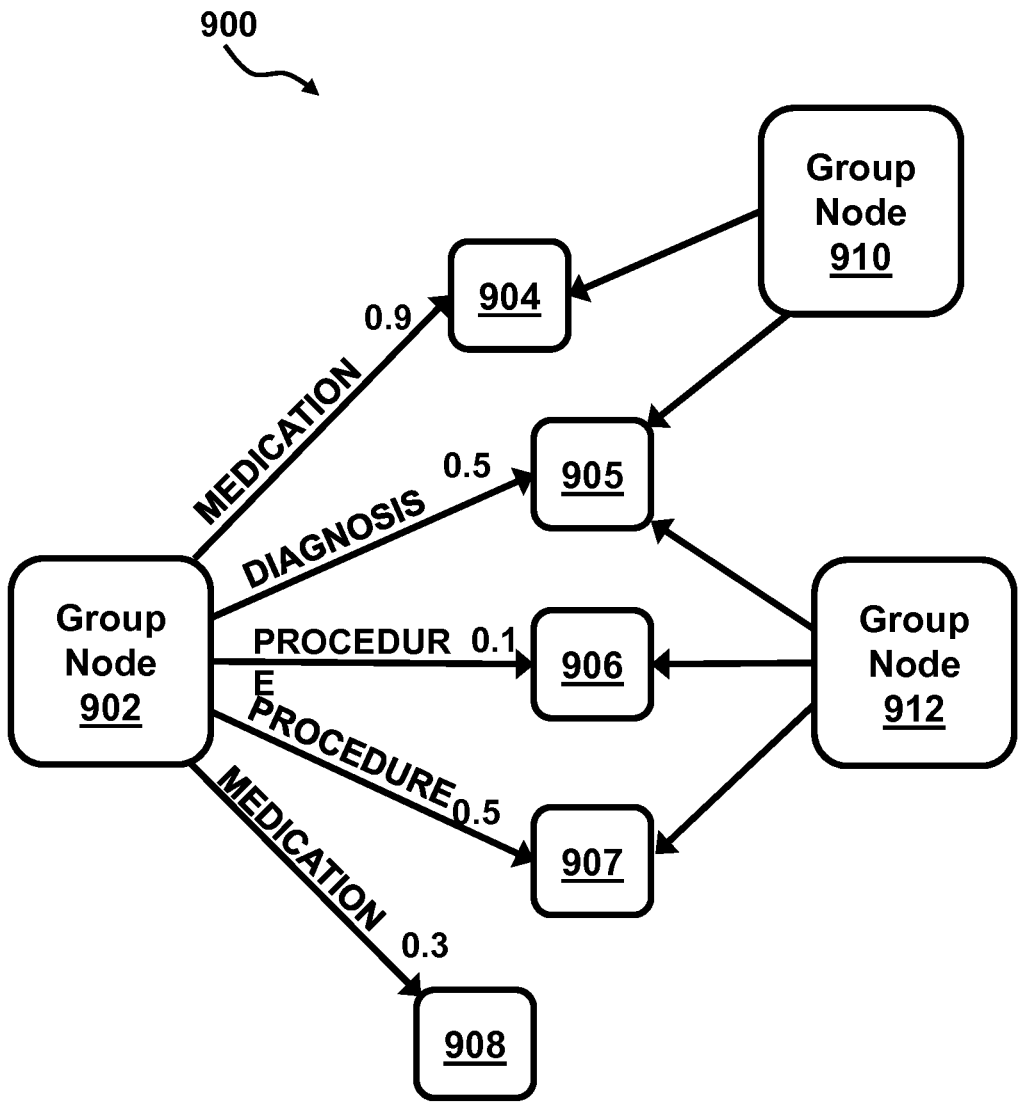
FIG. 9 is a second example weighted graph that utilize group nodes.

FIGS. 8 and 9 show example weighted graphs that utilize group nodes. As shown in FIG. 8, graph 800 includes a set of group nodes 802, 804, 806, 808, and 810 representing the current visit of a patient (802) and various other medical visits (804, 806, 808, 810), with weighted connections between current visit 802 and the previous visits. Additionally as shown, visit nodes 804, 806, 808, and 810 of graph 800 each include weighted connections to various pieces of medical information (812-829) based on predefined criteria. In some cases, a system may identify particular pieces of information from a graph like that shown in FIG. 8. For example, if the system selects medical information for which both the visit weight (the weight from the current visit to the visit with which the information is associated) and the information weight (from the visit to the information) are greater than 0.4, then the program might select information 816, 817, 819, and 827. As another example, if the system identifies information for which the information weight is greater than 0.5 and for which the number of available information nodes for the visit is less than 5, then the system might select information 813, 814, and 827 as relevant. In other cases, a system may utilize a graph like that illustrated in FIG. 8 to identify visits of interest rather than specific information. For example, if a system selects visits with a visit weight greater than 0.5, then the system might select visits 806, 808, and 810. As another example, if the program selects visits for which the sum of weights for all information nodes associated with the visit is greater than 1.0, then the program might select visits 804 and 808.

As shown in FIG. 9, graph 900 includes a group node 902 connected to several information nodes (904-908) by directed weighted connections. For example, group node 902 could represent a physician that a patient has seen, with each information node representing a piece of information that was recorded by the physician. In the example of FIG. 9, each edge also has an identifier (e.g., a relationship between the nodes, description of the child node, etc.) associated with the connection. Various types of identifiers may be used to categorize the connections as an additional level of complexity for the graph. FIG. 9 shows an example in which the identifiers describe the type of information that is represented by each child node. In particular, information 904 and 908 may describe medications prescribed to a patient, information 905 may be a diagnosis given to the patient, and information 906 and 907 may represent procedures performed on the patient. Therefore, if a system is identifying medications with an information weight higher than 0.4, then the system may select information 904 as the only medication information meeting the criteria. Through a combination of weighting and categorical or type edges, a graph may allow the system to search by both numerical and categorical variables.

Also as shown in FIG. 9, some pieces of information may be associated with more than one group node. For example, if a patient is prescribed the same medication at each of several doctor visits, then group nodes representing each of the doctor visits would have references to the same information. In the particular example of FIG. 9, a second group node 910 and a third group node 912 also attach to information 904-907. In such a situation, the system may use the connection patterns to determine the relevance of the information. For example, a prescription or diagnosis that is repeated over several doctor visits or by several doctors may be an important or likely relevant information.

Figure 6:
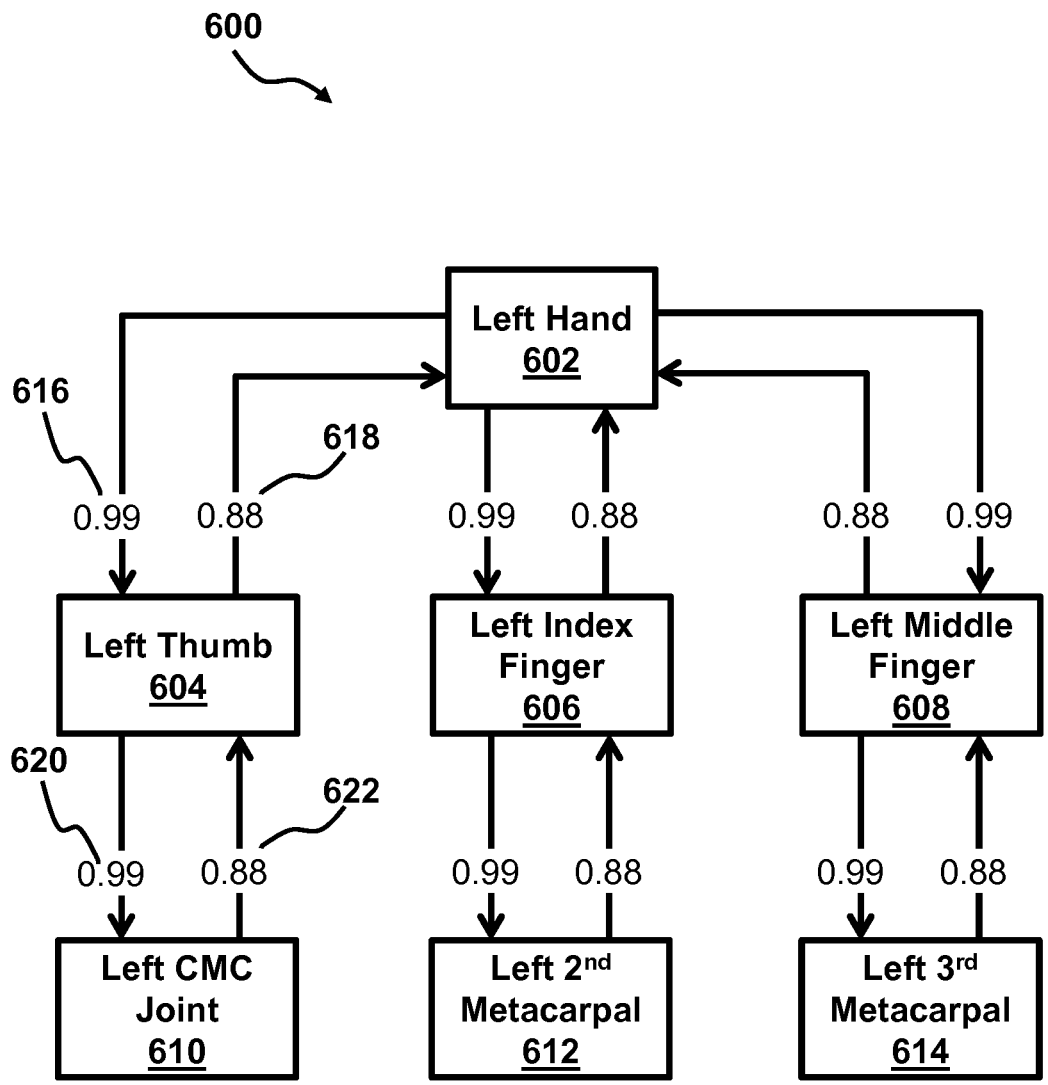
FIG. 6 is a block diagram representing a portion of a weighted graph according to an orthopedic example.

Programmatically, a weighted graph may be implemented in various ways. For example, as shown in FIGS. 5 and 6, a weighted graph may include nodes of information and pointers, with each pointer associated with a weight. Such an implementation may be based on abstract data types, such as lists, maps, multimaps, trees, or graphs. Some computer-programming definitions of "graph" may include a particular value/pointer structure that is not necessary to the present embodiments. Accordingly, the present embodiments should not necessarily be limited to only this type of implementation. In other embodiments, like that shown in FIG. 7, the weighted graph may be implemented as a list of information/condition identifiers and a respective list of weights for each connection between the identifiers. Such an implementation may be based on tables, hashtables, arrays, sets, and/or multisets, in addition to any other present or forthcoming data structures. In practice, a complete table-based weighted graph may include an n×n matrix of weights (where n is the number of nodes) with a weight assigned to each potential connection between elements. In incomplete graphs, fewer values may be pre-computed with modifications and calculations made when a healthcare provider begins a patient exam with a review of the patient's current condition and historical patient information. In a non-limiting example, such a healthcare provider may be a nurse working with a patient before an encounter with the patient's primary care provider. When the healthcare provider inputs the new data, it may be used by the processor to complete or partially complete a previously incomplete graph for the patient. In some cases, pre-computed graphs are stored for later reference in, for example, a database. In this way, logic can be quickly applied to, for example, linked-graphs or other unchanged portions of graphs, potentially reducing computation time for a desired, more complete weighted graph to be used during the patient encounter.

In some cases, the weighted graph may store information regarding the relevance of information to particular caregivers that may receive the relevant information. For example, the placement of the current condition on the weighted graph may depend on the caregiver's identity. Such an embodiment may be implemented by assigning caregiver-specific nodes for each condition that relates to the caregiver. Alternatively, specific condition nodes (or whole weighted-graph sections) may be assigned to each caregiver. As another example, different weights may be applied to connections in the weighted graph based on which caregiver is seeking relevant information. Such an implementation may use separate weighted graphs for one or a set of caregivers. It should be noted that, in an exemplary embodiment, a caregiver is presented with the relevant medical information without necessarily seeking out the information. Hence, the identity of the caregiver "seeking information" would be assessed on the basis of which caregiver will be receiving the information. Additionally, the caregiver "identity" may be a specific personal identity (e.g., Dr. Smith), a particular specialty (e.g., ID=Oncologist), a medical facility (e.g., ID=Doctor at Four Pines Hospital), or any other identifier that the weighted graph may use to assess the relevance of patient information.

Although the information may be described as contained in a single weighted graph, the actual graph may be implemented as multiple weighted graphs or subgraphs containing some shared information. For example, one weighted graph may represent the general comparative relevance of various conditions, that is, the relevance for a general population of patients, without specific patient information. Such a general graph may be coupled to a graph of medical information for a particular patient so that each graph provides part of the connectivity between nodes. Additionally, patient information may be stored in multiple locations and, therefore, may be represented in separate subgraphs. In practice, one or more general graphs may be preloaded onto an accessing device so that the information contained therein may be accessed and combined with specific patient information that is downloaded when a user activates the programming. Additionally, breaking the full patient graph into smaller subgraphs may allow for more efficient access and storage, precluding the need to download the whole graph at once.

The combining of multiple information may be executed in various way. For example, the two weighted graphs may be connected so that nodes representing the same information/condition may be used as a single node with separate edges representing the weighting values from each of the graphs. In another implementation, the various weights that represent the connections between two particular nodes (i.e., different weights for the connection in each graph) may be aggregated (e.g., averaged, summed, multiplied, etc.) to produce single weight values for each connection. In yet another implementation, edges may be established between the nodes of the separate graphs in order to represent different levels of connectivity between similar or equivalent nodes in different graphs.

In order to determine a relevance score for the historical patient information with respect to the current condition, a system may input a numerical value into the weighted graph at the node representing the historical patient information and then calculate the effect of the input value at the node representing the current condition. For illustration, take the example of condition 502 ("Heart Attack") as the current condition, and conditions 504 ("High Blood Pressure") and 506 ("Broken Pelvis") are the preexisting conditions. To determine the relevance of information related to each preexisting condition, the system inputs a value (1, for instance) at the nodes for conditions 504 and 506 and calculates the effect of these inputs at the node for condition 502. For the example weights shown, the result would be:

$$\text{Relevance(High BP)}=\text{input}*\text{weight}=1*0.9=0.9$$

$$\text{Relevance(Broken Pelvis)}=\text{input}*\text{weight}=1*0.29=0.29$$

Accordingly, for a current condition of a heart attack, information regarding the patient's high blood pressure is significantly more relevant than information regarding the broken bones in the patient's pelvis.

In some cases, the system may treat some pieces of historical patient information as having a higher importance, independent of the current condition. For example, a very mild or long-past injury to the shoulder may be given less importance than a severe or recent injury to the thumb. Functionally, the system may implement such importance values by altering the numerical value that is input at the node associated with the historical patient information. For instance, taking the example of the heart attack and the weighted graph of FIG. 5, assume hypothetically that the patient's high blood pressure is right on the borderline between high and normal blood pressure. Assume also that the patient's broken pelvis is a recent and severe injury (i.e., severe enough to have formed a blood clot in a major artery). In this case, a value of 1 may be assigned to the high blood pressure, and a value of 4 may be assigned to the broken pelvis. With these new values, the relevance scores become:

Relevance(High BP)=input*weight=1*0.9=0.9

Relevance(Broken Pelvis)=input*weight=4*0.29=1.16

Accordingly, a very mild high blood pressure may be less relevant to a heart attack than the patient's recent and/or severe pelvic injury. In an embodiment, the system may either determine recentness of the injury (and adjust the input and/or weight values) at the time that the relevant information is requested. In addition, the system may occasionally adjust the weights automatically as time passes. As used herein, "occasionally" may mean periodically or it may mean in response to a certain occasion/event. In either interpretation, the system would be programmed to automatically respond to pre-specified time periods or events by updating the information in the graph.

In addition to the above example of the relevance of one piece of information being based on whether the weighting achieves a threshold score, other criteria may be used to determine relevance. For example, the number of "children" nodes that a condition or piece of information has in the graph may be used as a criterion for determining the relevance. In an example embodiment, a certain relevance search may require that a condition have more than three children nodes in order to be considered for relevance. Other relationships between weights, connections, and inputs may be used. As another example, the weights associated with the children, edges, and/or parent nodes of a particular condition may be combined to compare to a threshold. As a particular implementation, a threshold for relevance could be that the sum of all children nodes for a piece of information must be greater than a certain amount in order to be considered relevant.

Although the above example includes direct links from the patient information to the current condition, the relevance score may be calculated for indirect movements as well. However, some complexity may be added in such a case due to the possibility of multiple paths having different weights. For example, to find the relevance of a past knee surgery on a current heart attack, a pathway may go through the nodes for either High Blood Pressure, Smoker, or Broken Pelvis. To correct for this issue, some embodiments may adjust the weights to be conservative (each path from one node to a second node has the same weight). Alternatively, the system may simply avoid determining a relevance score for historical patient information that does not connect directly to the current condition. As another alternative, the system may test all shortest routes to determine which route is most relevant. In the particular case, the relevance scores would be:

Relevance(Knee Surgery)=
    input*weight1*weight2=1*0.12*0.90=0.11

Relevance(Knee Surgery)=
    input*weight1*weight2=1*0.79*0.29=0.23

Relevance(Knee Surgery)=
    input*weight1*weight2=1*0.06*0.82=0.05

Therefore, the maximum relevance of the knee surgery would be 0.23.

As shown at block 308, method 300 may also include prominently presenting the historical patient information based on the relevance score. Like block 304, the presenting of information, as represented at block 308, is optional and need not be performed in an exemplary embodiment. Presenting the patient information may take several forms. For example, the information may be included in a graphical user interface (GUI) and output to a display, such as display 110. In such an example, system 102 may generate the GUI internally and output the generated GUI to display 110 through an integral, local, remote, or indirect network. As another example, system 102 may output the relevance data to a separate system that designs and outputs the GUI. In some cases, the relevant information and/or designed GUI may be stored in memory for retrieval by a caregiver. Display device 110 may not be a simple monitor or other basic display device. Rather, the system 102 may output relevant information to any computing device, portable device, wearable device, audio presentation system (as an audio user-interface rather than a GUI), collection of displays, or other display system/device. Presenting may refer to storing, displaying, transmitting to external systems, or presenting via audio, touch, or symbolic representation.

A system may use any of several ways to determine whether the relevance score associated with a piece of historical patient information is relevant enough to be presented, and how prominently the information should be presented. In one embodiment, a simple threshold relevance level may be assigned and compared to the relevance level of the one or more pieces of patient information. In such a case, all information with a relevance score higher than the threshold may be presented. In order to determine how prominently the information is presented, a system may have multiple predetermined thresholds, which each define a different level of prominence for the presentation of information.

In another embodiment, a maximum and/or minimum number of information elements to be presented may be defined. For example, a system may pre-assign a portion of a GUI for historical patient information and also define a number of pieces of information, n, that may be represented in the portion. In this case, the information may be ranked according to relevance score, and the top n pieces of information are selected regardless of whether the relevance scores exceed a threshold.

In some embodiments, a GUI or other medium of presentation may include elements other than the relevant medical information. A system may, in some embodiments, assign a relevance value for the other information on the presentation medium. Based on the assigned relevance of the other information, the system may select the threshold(s) for determining relevance or the maximum/minimum number of conditions to present. For example, the additional information could be included alongside the preexisting condition information, so that the most relevant information may be presented regardless of whether it is medical information or other information.

In addition to using a graph to score and present relevant information. A system may use the weighted graph in other ways to assist a caregiver or patient. For example, the system may allow a user to view and/or modify the contents of the weighted graph itself. For example, an interface may be provided to show some or all of the patient's weighted graph (e.g., in the formats shown in FIGS. 4-7 or other forms) to a user. Then, the user may choose to modify parameters, weights, or information in the weighted graph directly in either the same or a different accessible interface. In this way, a caregiver can see what is causing particular information to be presented frequently or a user can see what information is being presented to his or her caregivers. In some cases, the identity of the caregiver may influence the presentation of the historical patient information. As discussed above, one or more caregiver identities may be used in the weighted graph for assessing relevance of information. Alternatively, the system may use caregiver identity to filter information for which relevance has already been determined in accordance with the weighted graph. As an example situation, if the caregiver is a specialist in some area of medicine, then the information from that specialty may be presented more prominently than similarly relevant information form another field of medicine. As another example, the system may store a set of user-preferences that define a relative prominence for certain information according to the desired workflow outlined by the caregiver. Such user-preferences may be stored as a user-profile in the system. Facility-wide, department-wide, or team-wide preferences may also be assigned on a profile basis to members of each respective group. In general, the smaller-group rules would supersede the general or large group preferences.

B. Constructing and Adjusting the Weighted Graph

In order to use the weighted graph for determining relevance, the weighted graph may need to be constructed based on the relationships between medical conditions and other potentially relevant information. Such a process is often imprecise, because the actual causal link between one condition and another is difficult to assess. However, the system may design the weighted graph intelligently based on experience, known medical principles, and continued adjustment. Regarding the experience-based construction and the known medical links between conditions, these values may be initially assessed and evaluated by a human caregiver, and input into the system. In other cases, the system may include automated agents/crawlers programmed to navigate through scholarly documents in search of terms representative of one of the conditions in the weighted graph. The agent may then use semantic text-recognition to detect connections between conditions. For example, if two conditions are mentioned in the same article with linking words such as "causal" or "correlated" in close proximity to descriptions of each condition, then the agent may return a tally of one positive mention between the two conditions. The system may react to such a transmission by increasing the weight between the two conditions.

Aside from the known or experienced connections, the system may use continuing streams of data to adjust the base model to better fit real connections between conditions. In an automated approach, such a process may incorporate machine learning algorithms as known to those of skill in the art. One simple technique may be to increase the weight between two conditions in response to determining that the conditions often occur in the same patients. As a refinement to this simple technique, a system may more-heavily respond to cases in which the conditions are diagnosed or treated in temporal proximity (i.e., both conditions manifested at roughly the same time). Additional importance may be given to the first condition if it rarely occurs in patients that do not have the second condition. As discussed above with respect to descendent/ancestor relationships, the relative weight of ancestor condition (either more central than or potentially causal of the descendant condition) may be higher than that of a descendent condition.

Although the present descriptions relate generally to finding relevant information by experienced medical professionals, the system may also be beneficial for non-professionals. For example, if a new physician or non-physician is attempting to learn about particular conditions or treatments associated with their own symptoms or the symptoms of another person, the weighted graph may be used to locate and rank relevant information. For example, a new doctor attempting to diagnose a patient that has information stored within the weighted graph may input various symptoms and/or lab tests to see which conditions may be associated with the expressed symptoms or patient history. Since the system may be constantly learning and gathering relevance scores from a variety of sources, the new physician may find the most likely set of possible conditions and treatments as rated and modified by other professionals. Hence, a hospital may train the new doctor by providing access to such a weighted graph system and letting the doctor learn as he works. Additionally, as the doctor assesses treatments, the program may bring up potential or likely side effects, reactions, and value of the various treatments so that the doctor is better prepared to answer patient questions.

As another example use for the present embodiments, a researcher may use the collected relevance information, from the weighted graph, to recognize and establish particular connections or trends relating to the connected conditions. For example, if two different conditions often coincide, then, based on this data, the researcher could drive investigations towards determining a correlation or cause for the connection between the conditions. As another example, if one physician often has patients that receive a certain rare diagnosis, then a hospital administrator may recognize this connection through relevance processing and respond accordingly. Other examples may be used.

Another technique by which the weight of an edge may be adjusted is to monitor user-interactions with provided relevance information. As discussed above, a caregiver may be presented with information that the system deems relevant to a current condition. After presenting the information, the system may receive indications as to whether the caregiver selected the presented items for further review or diagnosis. If the caregiver did select the presented information, then the system may adjust the weighted graph to increase the weight of the edge between the selected information and the current condition for which the caregiver was searching. Such a process may also be used for training the original weighted graph, outside of any real medical situation. For example, a set of medical professionals may be presented with current conditions and potentially relevant historical patient information and/or potential diagnoses as part of a graph-building or graph-refining process. Then, the professionals may rate (on a yes/no, continuous or discrete scale, etc.) the relevance of the presented information.

III. Example Embodiment: Orthopedics

This example is given for illustration and should not be seen as limiting the scope of the disclosed embodiments.

In one example embodiment, the present methods, media, and systems may be used for recognizing relevant orthopedic medical history in accordance with current orthopedic conditions. The main structure of interest in orthopedics is the skeletal system and the joints, musculature, and ligaments that support the skeletal system. Accordingly, the structure of a weighted graph for determining relevant information for an orthopedic application may relate to the structure of the skeletal system. In particular, edges that connect nodes representing physically connected bones/muscles may be weighted more heavily than edges between nodes representing bones that are separated from one another.

FIG. 6 shows an example portion 600 of a weighted graph that includes some elements for an orthopedic representation of a patient's left hand. As shown, the group may be represented by the general node 602, "Left Hand," that connects with three less general nodes ("Left Thumb" 604, "Left Index Finger" 606, and "Left Middle Finger" 608), which in turn connect to three more specific nodes ("Left CMC Joint" 610, "Left $2^{nd}$ Metacarpal" 612, and "Left $3^{rd}$ Metacarpal" 614). As shown, weighted graph 600 is directional and incomplete. However, a complete version of such a system is possible and indeed has been designed for a full skeletal system by the present inventor. For each connection (edge) in graph 600, a weight (e.g., weights 616, 618) is defined, representing a relative relationship between the anatomy represented by the nodes around the edge. Because of the directional weighting, different relevance levels may be assessed depending on the directionality of the relevance determination. For example, weight 616 may be applied to determine the relevance of patient information associated with node 602 to a current condition at node 604, and weight 618 may be applied to determine the relevance of patient information associated with node 604 to a current condition at node 602.

As discussed above, nodes that represent appendages to the central skeletal structure may be represented by descendant nodes in a hierarchal arrangement. Since an injury to the second metatarsal bone may be generalized as an injury to the left index finger or as an injury to the left hand, node 612 may be seen as a descendant of nodes 606 and 602. Similar hierarchal relationships may be formed for nodes representing each part of the body's skeletal system based on the connectivity of the anatomy (e.g., phalanges connected to the metatarsals, metatarsals connected to the talus, etc.) Accordingly, a full hierarchy of skeletal components may be represented as a weighted graph and used to determine relevance of a preexisting orthopedic condition on a current orthopedic condition.

As discussed in an earlier section, ancestor nodes may have a more relevant effect on their descendant nodes than the descendant nodes have on the ancestors. FIG. 6 shows such relationships through the directional weighting. In particular, the relevance of a left hand injury (ancestor node 602) on a left CMC joint injury (descendant node 610) is shown to be:

Relevance($L$·Hand to $L$·CMC Joint)= weight616*weight620=(0.99)*(0.99)=0.98

In contrast, the relevance of a left CMC joint injury on the left hand as a whole would be:

Relevance($L$·CMC Joint to $L$·Hand)= weight622*weight618=(0.88)*(0.88)=0.77.

In other embodiments, descendants may be weighted the same or even higher than ancestor nodes to capture particular relationships.

In addition to ancestor and descendent relationships, other hierarchal positions may be defined throughout a skeletal system. For instance, an edge between the left thumb (node 604) and the left index finger (node 606) may be defined as "adjacent," because the body parts represented are connected but neither is more general or central than the other (i.e., neither is a true ancestor to the other). As another example, an edge between a left thumb and a right thumb may define each node as "contralateral" to the other, because the two thumbs are at the same hierarchical level, but oriented on the opposite side of the body. As still another example, a right hand node may be identified as a "contralateral ancestor" node to the right thumb, because the right hand is contralateral to an ancestor of the left thumb.

FIG. 7 shows an example relevance chart for different anatomy related to the "Left Arm." As shown, different weights and relationship types may be defined for each anatomical part with respect to the left arm. Although the weights shown may be preferable, other example values may be used. In the example of FIG. 7, if a patient has a preexisting injury to the left arm, and has a current injury to the right scapula, then the relevance of the preexisting injury may be assessed as 0.48 (importance value), where the importance value relates to the severity or recentness of the preexisting injury.

In the subject description, the word "exemplary" is used to mean serving as an example, instance or illustration. Any embodiment or design described herein as "exemplary" is not necessarily to be construed as preferred or advantageous over other embodiments or designs. Rather, use of the word exemplary is intended to present concepts in a concrete manner. Accordingly, all such modifications are intended to be included within the scope of the present disclosure. The order or sequence of any process or method steps may be varied or re-sequenced according to alternative embodiments. Any means-plus-function clause is intended to cover the structures described herein as performing the recited function and not only structural equivalents but also equivalent structures. Other substitutions, modifications, changes, and omissions may be made in the design, operating conditions, and arrangement of the preferred and other exemplary embodiments without departing from scope of the present disclosure or from the scope of the appended claims.

What is claimed is:

1. A non-transitory computer-readable medium having stored thereon instructions executable by a processing system to cause the processing system to perform functions comprising:

receiving data indicative of a patient identity of a patient and a current condition;

in response to receiving the data indicative of the patient identity and the current condition, transmitting a request for historical patient information, and wherein the historical patient information is received in response to the transmitted request;

dividing the historical patient information into a plurality of classifications, wherein at least one of the plurality of classifications is representative of a past diagnosis of the patient;

using a weighted graph unique to the patient to determine a weight between the past diagnosis and the current condition;

using the weight and an input value to determine a relevance score of the past diagnosis to the current condition;

determining a level of prominence with which to display the historical information based on the relevance score, wherein determining the level of prominence comprises comparing the relevance score to a plurality of thresholds, and wherein each threshold of the plurality of thresholds defines a different level of prominence for displaying the historical patient information; and displaying the historical patient information on a graphical user interface in accordance with the determined level of prominence such that historical patient information satisfying a first threshold of the plurality of thresholds is displayed in a first manner and historical patient information satisfying a second threshold of the plurality of thresholds is displayed in a second manner.

2. The non-transitory computer-readable medium of claim 1, wherein the current condition comprises a primary concern for a medical visit of the patient.

3. The non-transitory computer-readable medium of claim 1, wherein the functions further comprise:
detecting a change in relevance of the past diagnosis to the current condition; and
responsively modifying the weighted graph to change the weight in accordance with the detected change in relevance.

4. The non-transitory computer-readable medium of claim 3, wherein detecting the change in relevance comprises detecting user-selection of presented indicia, and wherein the weighted graph is responsively modified to increase the weight between a previous condition and the current condition.

5. The non-transitory computer-readable medium of claim 1, wherein the functions further comprise identifying an undiagnosed condition that has a high relevance with respect to (i) other preexisting conditions associated with the patient and (ii) the current condition; and creating a second relevance score between at least the undiagnosed condition and the current condition.

6. The non-transitory computer-readable medium of claim 5, wherein the functions further comprise:
detecting that the patient has received a second past diagnosis associated with the undiagnosed condition; and
in response to the detecting, modifying the weighted graph to increase the second relevance score.

7. The non-transitory computer-readable medium of claim 1, wherein the weighted graph defines, for each respective connection between any two nodes in the weighted graph, a single respective weight, and wherein edges in the weighted graph are directionally dependent.

8. The non-transitory computer-readable medium of claim 1, wherein the relevance score comprises an output value, at a node associated with the current condition in the weighted graph, resulting from an input value at a node associated with the historical patient information in the weighted graph.

9. The non-transitory computer-readable medium of claim 1, wherein the functions further comprise determining the input value based on one or more of a severity and a recentness associated with the past diagnosis.

10. The non-transitory computer-readable medium of claim 1, wherein weight values of edges in the weighted graph are determined in accordance with known medical relationships between medical conditions.

11. The non-transitory computer-readable medium of claim 10, wherein the known medical relationships comprise hierarchical connections, wherein the hierarchical connections comprise ancestor connections, descendent connections, and adjacent connections.

12. The non-transitory computer-readable medium of claim 1, wherein the functions further comprise receiving a second input value from an input device, and in response to the receiving of the second input value, updating the relevance score based on the second input value and the weight.

13. The non-transitory computer-readable medium of claim 1, wherein the functions further comprise:

using the weighted graph unique to the patient to determine a second weight between the past diagnosis and the current condition; and
using the weight, the second weight, and an input value to determine the relevance score.

14. The non-transitory computer-readable medium of claim 1, wherein the functions further comprise:
receiving a caregiver identity; and
determining the level of prominence with which to display the historical information further based on the caregiver identity.

15. The non-transitory computer-readable medium of claim 1, wherein the functions further comprise:
determining a source that established the past diagnosis of the patient; and
automatically adjusting the weight between the past diagnosis and the current condition based on the source that established the past diagnosis of the patient.

16. A method comprising:
receiving, at a processing system, data indicative of a patient identity of a patient and a current condition;
receiving information indicative of historical patient information associated with the patient identity,
dividing the historical patient information into a plurality of classifications, wherein the current condition and plurality of classifications are each represented by respective nodes in a weighted graph unique to the patient;
the processing system using the weighted graph to determine a weight, wherein the weight correlates to an edge between one of the plurality of classifications to the current condition;
the processing system using the weight and an input value to determine a relevance score, wherein input value correlates to a relationship between the plurality of classifications to the current condition;
the processing system determining a level of prominence with which to display patient information based on the relevance score, wherein determining the level of prominence comprises comparing the relevance score to a plurality of thresholds, and wherein each threshold of the plurality of thresholds defines a different level of prominence for displaying the patient information; and
the processing system causing display of at least a portion of the patient information on a graphical user interface in accordance with the determined level of prominence such that patient information satisfying a first threshold of the plurality of thresholds is displayed in a first manner and patient information satisfying a second threshold of the plurality of thresholds is displayed in a second manner.

17. The method of claim 16, further comprising:
detecting user-selection of the patient information on the graphical user interface; and
responsively modifying the weighted graph to increase the weight of the edge between one of the plurality of classifications and the current condition in accordance with the detected user selection of the patient information.

18. A processing system comprising:
a computer-readable medium;
a communication interface communicatively coupled to the computer readable medium; and
a processor communicatively coupled to the computer-readable medium and the communication interface, wherein the processor is configured to:

receive data indicative of a patient identity of a patient and a current condition;

receive information indicative of historical patient information associated with the patient identity;

divide the historical patient information into a plurality of classifications, wherein the current condition and plurality of classifications are each represented by respective nodes in a weighted graph unique to the patient;

use the weighted graph to determine a weight representing a relevance of one of the plurality of classifications to the current condition wherein the weight correlates to an edge between one of the plurality of classifications to the current condition;

use the weight and an input value to determine a relevance score, wherein the input value correlates to a relationship between the one of the plurality of classifications;

determine a level of prominence with which to display the plurality of classifications based on the relevance score, wherein determining the level of prominence comprises comparing the relevance score to a plurality of thresholds, and wherein each threshold of the plurality of thresholds defines a different level of prominence for displaying the plurality of classifications; and present the plurality of classifications on a graphical user interface in accordance with the determined level of prominence such that classifications satisfying a first threshold of the plurality of thresholds is displayed in a first manner and classifications satisfying a second threshold of the plurality of thresholds is displayed in a second manner.

19. The processing system of claim 18, wherein the processor is further configured to:

detect user-selection of the presented indicia; and responsively modify the weighted graph to increase the weight of an edge between the historical patient information and the current condition in accordance with the detected user selection of the presented indicia.

20. The processing system of claim 18, wherein the relevance score comprises an output value, at a node associated with the current condition in the weighted graph, resulting from an input value at a node associated with the historical patient information in the weighted graph.

\* \* \* \* \*